United States Patent [19]
DeGroot

[11] Patent Number: 6,063,749
[45] Date of Patent: May 16, 2000

[54] STABILIZED ALKYL BROMIDE SOLVENTS CONTAINING DIALKYL CARBONATES

[75] Inventor: Richard J. DeGroot, West Lafayette, Ind.

[73] Assignee: Great Lakes Chemical Corporation, West Lafayette, Ind.

[21] Appl. No.: 09/112,958

[22] Filed: Jul. 9, 1998

Related U.S. Application Data

[60] Provisional application No. 60/052,035, Jul. 9, 1997.

[51] Int. Cl.[7] .............................. C23G 5/028; C11D 7/30; C11D 7/50; B08B 3/08
[52] U.S. Cl. .............................. 510/412; 134/40; 134/42; 252/364; 570/102
[58] Field of Search .......................... 510/412; 570/102; 134/42, 40; 252/364

[56] References Cited

U.S. PATENT DOCUMENTS

| | | | |
|---|---|---|---|
| 3,730,904 | 5/1973 | Clementson et al. | 252/171 |
| 4,018,837 | 4/1977 | Archer et al. | 260/652.5 R |
| 4,257,828 | 3/1981 | Wada et al. | 148/6.16 |
| 4,351,973 | 9/1982 | Ishibe et al. | 570/104 |
| 4,992,604 | 2/1991 | Reich et al. | 570/110 |
| 5,492,645 | 2/1996 | Oshima et al. | 252/171 |
| 5,541,221 | 7/1996 | Garst | 514/461 |
| 5,552,080 | 9/1996 | Bolmer | 510/412 |
| 5,616,549 | 4/1997 | Clark | 510/412 |
| 5,665,170 | 9/1997 | Lee et al. | 134/19 |
| 5,665,172 | 9/1997 | Oshima et al. | 134/40 |

FOREIGN PATENT DOCUMENTS

| | | |
|---|---|---|
| 0 609 004 A1 | 3/1994 | European Pat. Off. . |
| 1952784 | 8/1970 | Germany . |
| 1936987 | 2/1971 | Germany . |
| 53-127404 | 11/1978 | Japan . |
| 56-55322 | 5/1981 | Japan . |
| 1230312 | 4/1971 | United Kingdom . |
| 97/16583 | 5/1997 | WIPO . |

OTHER PUBLICATIONS

1230312 GB Archer et al. Apr. 28, 1971.

*Primary Examiner*—Christine Skane
*Attorney, Agent, or Firm*—Woodard, Emhardt, Naughton Moriarty & McNett

[57] ABSTRACT

This invention provides a stabilized alkyl bromide based solvent system that is useful for cleaning and degreasing a wide variety of metal objects. The solvent is stabilized with a stabilizer system that includes a dialkyl carbonate such as dimethyl carbonate and optionally other stabilizers and/or acid scavengers to inhibit the metal induced decomposition of the alkyl bromide based solvent. The stabilized solvent is applied to metal articles by any known or conventional means to solvate and entrain greases, oils and other undesirable matter from the article's surface.

21 Claims, 1 Drawing Sheet

STABILIZED ALKYL BROMIDE SOLVENTS CONTAINING DIALKYL CARBONATES

REFERENCE TO RELATED APPLICATION

This application claims priority to a now abandoned U.S. Provisional Application serial No. 60/052,035 filed on Jul. 9, 1997 by Richard J. DeGroot.

FIELD OF THE INVENTION

This invention relates to a stabilized alkyl bromide based solvent that can be used as a cleaning solution for metal articles. More specifically the present invention is directed to an alkyl bromide based solvent stabilized with a dialkyl carbonate and optionally other stabilizers and/or acid scavengers and to a method of cleaning a metal article with the stabilized alkyl bromide solvent.

BACKGROUND OF THE INVENTION

There is a demand to find new cleaning and degreasing solvents to replace chlorinated hydrocarbons and chlorofluorocarbons. Cleaning and degreasing solvents are used to remove greases, oils, dirt and other undesired particles that accumulate on surfaces of metal articles during manufacture or repair of the articles. Typically the article is either sprayed with the solvent, submerged in a "dip tank" containing the solvent, or treated with hot vaporized solvent in a vapor degreasing chamber. After the solvent has been removed from the cleaned article, it can be shipped to the consumer or further processed in a subsequent operation. Chlorinated hydrocarbon and chlorofluorocarbon solvents have enjoyed wide use by metal fabricating industries especially the aerospace and electronic manufacturing industries as cleaning and degreasing solvents. These solvents have high solvating ability, are low boiling, and are relatively inexpensive to produce. However, in recent years use of these solvents has been restricted because of their toxicity and environmental hazards, particularly in light of the link between use of these solvents and destruction of the atmospheric ozone layer. Because alkyl bromides have not been found to be as detrimental to the environment, these solvents are rapidly replacing chlorinated hydrocarbons and chlorofluorocarbons as the preferred solvents for cleaning and degreasing operations.

Alkyl bromide solvents were not traditionally exploited as cleaning solvents primarily because of their high cost relative to the chlorinated hydrocarbons and chlorofluorocarbons. Furthermore, alkyl bromides readily react with metals such as aluminum, magnesium, copper, zinc, iron, titanium, tin and alloys of these metals that are commonly used to manufacture industrial components. Metal induced decomposition generates metal bromides, bromide salts and hydrobromic acid as some of the bromine decomposition species. Generation of these decomposition species is harmful to the metal articles. The metal bromides and some of the bromide salts are formed from metal ions leached from the metal, and the hydrobromic acid severely corrodes metals, further exacerbating the problems associated with using alkyl bromides as cleaning and degreasing solvents. Furthermore, these decomposition species often adhere to the metal surface, defeating the cleaning process.

SUMMARY OF THE INVENTION

The present invention provides a stabilized alkyl bromide solvent that comprises a metal stabilizer system designed to inhibit metal induced decomposition of the alkyl bromide. The metal stabilizer system includes a dialkyl carbonate as a stabilizer component. Optionally, additional stabilizer components such as ethers, alcohols nitroalkanes and epoxides are included in the metal stabilizer system. The stabilizer system included in the solvent inhibits reactive metals, particularly aluminum, iron, and copper, from decomposing the alkyl bromide solvent even at elevated temperature and thus prevents formation of decomposition products such as metal bromides, bromide salts and hydrobromic acid. In addition, the alkyl bromide solvent can also include acid scavengers to prevent residual acid in the solvent from corroding metal articles.

The present invention also provides a method for cleaning a metal article using the stabilized alkyl bromide solvent. The solvent is applied to the metal article by any of the known or conventional methods to solvate and entrain grease, oils, and dirt adhering to the metal surface. Removal of the contaminated solvent provides a cleaned article that is suitable for subsequent processing or forwarding to consumers.

DETAILED DESCRIPTION OF THE INVENTION

Figure 1:
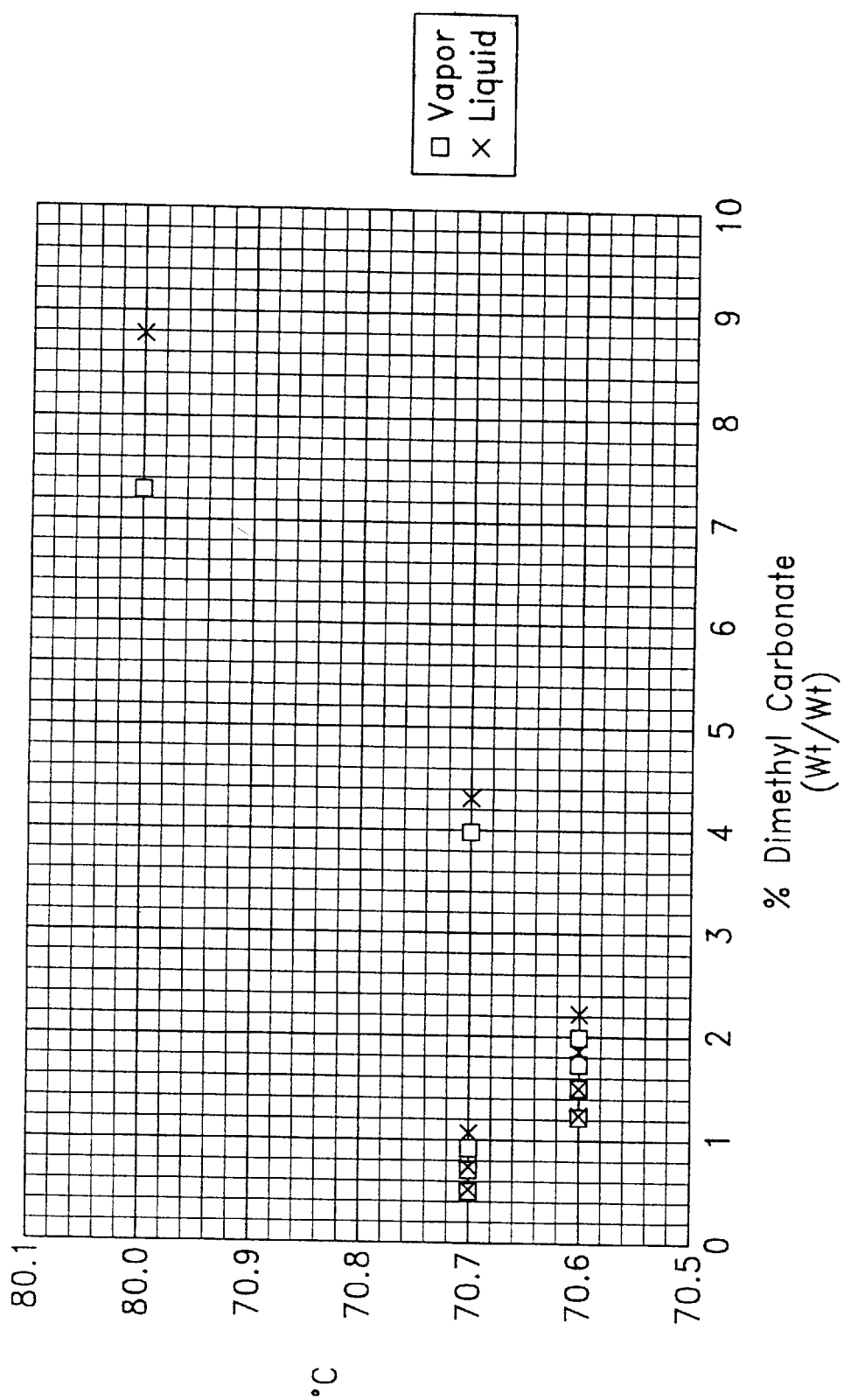
FIG. 1 is a plot of 1-bromopropane concentrations in the vapor and liquid states during distillation of a stabilized 1-bromopropane based solvent.

This invention is directed to a stabilized alkyl bromide solvent that is useful as a cleaning and degreasing solvent. The solvent contains a metal stabilizer system that inhibits metal induced decomposition of the alkyl bromide even at elevated temperatures. The stabilizer system includes a dialkyl carbonate. Optionally the metal stabilizer system includes stabilizer components such as ethers, alcohols, nitroalkanes and epoxides that can be added to tailor the stabilized solvent to specific applications. The stabilized solvent can include additional components such as acid scavengers, surfactants, co-solvents and miscibility agents.

Use of the stabilized alkyl bromide solvent in accordance with this invention provides several advantages over other known degreasing solvents. Alkyl bromides are more environmentally friendly, and their use has not been severely restricted by government regulations. The stabilizer system, specifically the dialkyl carbonates, co-distill with the alkyl bromide solvent so when the stabilized solvent is used in a vapor degreaser, the dialkyl carbonate does not concentrate in either the vapor or liquid phase. Dialkyl carbonates have low water solubility; so the stabilizer concentration in the stabilized solvent is not significantly diminished by water extraction, for example, in vapor degreasing systems that use a water separator to remove water-soluble impurities from the decreasing solvent.

The stabilized solvent comprises an alkyl bromide having from three to five carbon atoms as a solvent. Preferably the solvent is a low boiling alkyl bromide to minimize the cost associated with refluxing the stabilized solvent in a vapor degreaser and to facilitate removing, the solvent from the metal article. The alkyl bromide components include, but are not limited to: 1-bromopropane, 2-bromopropane, 1-bromo-2-methylpropane, 2-bromo-2-methylpropane, 1-bromobutane, 2-bromobutane, 1-bromopentane, 2-bromopentane, 3-bromopentane, 1bromo-2-methylbutane, 1-bromo-3-methylbutane, 2-bromo-2-methylbutane, 2-bromo-3-methylbutane, 1-bromo-2,2-dimethylpropane, and mixtures thereof. The preferred solvent is 1-bromopropane because of its low toxicity, low boiling point and generally benign effect on the environment.

The stabilized solvent also comprises up to about 15% of a metal stabilizer system, more preferably up to about 4%, most preferably up to about 2% by weight. The metal stabilizer system includes a dialkyl carbonate of the formula $(R_1O)(R_2O)C(O)$. The $R_1$ and $R_2$ substituents independently are $C_1$ to $C_5$ alkyls. As little as 0.01% by weight dialkyl carbonate inhibits metal induced decomposition of the alkyl bromide solvent. Addition of greater amounts of dialkyl carbonate, e.g., up to about 15% by weight or more, is not detrimental to the solvent's stability or its cleaning and degreasing ability. The dialkyl carbonates are only slightly soluble in water, and thus, this metal stabilizer system has a water extractability from the cleaning solvent of not more than about 10% by weight. Specific examples of dialkyl carbonates that are useful in the present invention include, but are not limited to: dimethyl carbonate, diethyl carbonate, dipropyl carbonate, methyl ethyl carbonate, methyl propyl carbonate and mixtures of these carbonates. The preferred dialkyl carbonate for the present invention is dimethyl carbonate.

The metal stabilizer system can include additional stabilizer components. The components include ethers, alcohols, nitroalkanes, epoxides and combinations of these stabilizer components.

Specific examples of ethers that can be added to the stabilized solvent include: diethyl ether, diisopropyl ether, dibutyl ether, methyl t-butyl ether, 1,4 dioxane, 1,3 dioxalane, trioxane, γ-butyrolactone, tetrahydrofuran, acetal, dimethyl acetal, dialkyl ethers of ethylene glycol, e.g. dimethyl ethylene glycol ether, diethyl ethylene glycol ether, and monoalkyl ethylene glycol ethers sold under the trade name CELLOSOLVE that have from 1 to 10 carbons such as methyl cellosolve, ethyl cellosolve, and isopropyl cellosolve. These ethers are added singly or as mixtures of two or more to the stabilized solvent.

Examples of alcohols that can be added to the stabilized solvent include: ethyl alcohol, propyl alcohol, iso-propyl alcohol, t-butyl alcohol, t-amyl alcohol, sec-butyl alcohol, phenols, e.g. phenol, p-cresol, m-cresol, o-cresol, amino alcohols, e.g. monoethanol amine, diethanol amine, triethanol amine, acetylene alcohols, e.g. methylbutynol, methylpentynol, benzotriazol, and mixtures of alcohols.

Typical nitroalkanes useful in the present invention include: nitromethane, nitroethane, 1-nitropropane, 2-nitropropane, nitrobutane, and mixtures of nitoalkanes.

Specific examples of epoxides useful with the present invention include: epibromohydrin, propylene oxide, 1,2-butylene oxide, 2,3-butylene oxide cyclohexene oxide, glycidyl methyl ether, glycidyl methacrylate, pentene oxide, cyclopentene oxide, and cyclohexene oxide. The epoxides are added to the stabilized solvent either singly or as a mixture of two or more.

The stabilized alkyl bromide solvent can include about 0.1% to about 5%, more preferably about 0.2% to about 0.5%, by weight of an acid scavenger. A wide variety of amines and epoxides are suitable for the present invention. The acid scavenger reacts with residual acid in the solvent and forms either a covalent or ionic bond with the acid. The residual acid can be from any source including from the decomposition of the alkyl bromide solvent. By reacting with the acid in the stabilized solvent, the acid scavenger prevents acids from corroding and pitting metals in contact with the solvent whether these metals are part of the article being washed or a part of a component in the washing system. Similarly to the stabilizer components, acid scavengers can be used singly or as a mixture of two or more.

Non-nucleophilic amines are preferred, and thus secondary and tertiary amines are desired. By way of example, amines useful for the present invention include: hexylamine, octylamine, 2-ethylhexylamine, dodecylamine, ethylbutylamine, hexylmethylamine, butyloctylamine, dibutylamine, octadecylmethylamine, triethylamine, tributylamine, diethyloctylamine, tetradecyldimethylamine, dibutylamine, diisobutylamine, diisopropylamine, pentylamine, N-methylmorpholine, isopropylamine, cyclohexylamine, butylamine, isobutylamine, dipropylamine, 2,2,6,6-tetramethylpiperidine, N,N-dimethyl-p-phenylamine, N,N-diethyl-p-phenylamine, diethylamine, aniline, ethylenediamine, propylenediamine, triethylamine, tetraethylenepentamine, benzylamine, dibenzylamine, diphenylamine, and diethylhydroxyamine. These amines are useful either singly or as a combination of two or more.

The epoxides that serve as acid scavengers can also serve as metal stabilizer components for the solvent. Examples of these epoxides are listed above.

The stabilized solvent is prepared by the admixture of the alkyl bromide and a sufficient amount of the stabilizer system to provide the desired concentration of stabilizer. The order of addition is not critical for this invention. When desired the acid scavenger, surfactants and co-solvents can be added. Typical surfactants useful for the invention include ionic and non-ionic surface active agents, for example, sulfonate salts, phosphate salts, carboxylate salts, fatty acids, alkyl phenols, glycols, esters and amides. Surface active agents also include ionic and non-ionic water displacement compounds such as tetraalkyl ammonium sulfonate, phosphate, carboxylate and bromide salts, aliphatic amino alkanols, fluorinated amino alkanols, and chlorinated amino alkanols. Examples of co-solvents include: saturated hydrocarbons, alkenes, alkynes, alcohols, ketones and esters. Again the order of addition used to prepare the solvent is not critical.

The metal stabilizer component of the present invention inhibits metal induced decomposition of the alkyl bromide. These metals include reactive metals that decompose alkyl bromides. The reactive metals that can be cleaned or degreased with the stabilized solvent in accordance with this invention include any metal that decomposes alkyl bromides. Typically, these metals induce hydrolysis and/or dehydrobromination of the alkyl bromides to provide metal bromides, bromide salts, and hydrobromic acid as decomposition products. Metal-induced decomposition of an alkyl bromide is detected by observing a drop in pH of the solvents gas evolution generally detected as bubbles on the metal surface, formation or deposition of solid on the metal surface, formation of solids, precipitate or haziness in the solvent, and discoloration of either the solvent or the metal surface. Specific examples of metals that react with alkyl bromides include: aluminum, zinc, iron, copper, magnesium, titanium and alloys of these metals.

The stabilized solvent and the included metal stabilizer system exhibit excellent stability when exposed to reactive metals for an extended period of time. The metal stabilizer system inhibits decomposition of the alkyl bromide, and thus, prevents corrosion of the metal article. The stabilized solvent is stable in the presence of reactive metals at ambient temperature and elevated temperatures such as the boiling point of the stabilized solvent mixtures.

Immersion of metals in hot or boiling stabilized solvent for extended time does not result in corrosion of the metal or provides significantly reduced corrosion. Since the stabilizer system inhibits decomposition of the stabilized solvent, acidic decomposition products that corrode metal articles are not generated. Furthermore, inclusion of acid scavengers that react with residual acids prevents these acids from corroding the metal article.

The stabilized solvent of the present invention is suitable for washing metal articles to remove grease, oils and dirt from the metal surface. The stabilized solvent may by applied to the metal article by any method known or commonly used to clean or degrease articles. For example, the metal surface may be wiped with an absorbent medium containing the stabilized solvent such as a cloth saturated with the stabilized solvent. The metal article can be submerged or partially submerged in a dip tank. The stabilized solvent in the dip tank can be either hot or cold, and the metal article can be submerged for extended periods of time. Alternatively the solvent can be sprayed on to the article or the article can be cleaned in a vapor degreasing chamber with either liquid or vaporized stabilized solvent.

When the solution is applied as a vapor, the solvent is typically heated in a solvent reservoir to vaporize the solvent; the vaporized solvent then condenses on the surface of the metal article. The condensed solvent solvates or entrains grease, oil, dirt, and other undesired particles that are on the surface of the article. The contaminated solvent drains into the solvent reservoir carrying the solvated and entrained material to the reservoir. Since only the stabilized solvent is vaporized, the grease, oil and dirt remain in the reservoir, and the article is continually flushed with non-contaminated solvent. Often the contaminated solvent is subjected to a water separator where the solvent is washed or extracted with water to remove any water-soluble contaminants. When the stabilized solvent prepared in accordance with this invention is subjected to water extraction such as in a water separator, the concentration of the stabilizer component in the stabilized solvent is not significantly diminished.

The following examples further illustrate the present invention and are not intended to be limiting in any manner.

EXAMPLE 1

1-Bromopropane Stabilized with Dimethyl Carbonate

A sufficient amount of dimethylcarbonate was admixed with 1-bromopropane to provide a stabilized solvent having the desired concentration measured in percent by weight based upon the total weight of the final solution. Thus for example, a 1-bromopropane solvent containing 0.2% by weight of dimethyl carbonate was prepared by admixing 2 g of dimethyl carbonate and 998 g of 1-bromopropane. The resulting stabilized 1-bromopropane solvents were compared with non-stabilized 1-bromopropane and solutions of 1-bromopropane containing compounds known to stabilize chlorinated hydrocarbons.

Stabilization Evaluation

The reactivity of a series of stabilized solvents to aluminum alloys was evaluated according to the standard test procedure in ASTM D2943-71T. Aluminum 1100 alloy coupons were completely immersed in beakers containing 1-bromopropane without a stabilizer system and solutions of 1-bromopropane stabilized with the stabilizers listed in Table 1. The aluminum coupon was then etched with a stainless steel scribe to expose non-oxidized aluminum to the solvents. The beakers containing the solvents and coupons were covered with parafilm and allowed to stand undisturbed at ambient temperature. The coupons were observed regularly, and indications of a reaction between the solvent and the coupon, such as gas evolution, solid formation and discoloration of the coupon or the solvent were noted. The times in minutes for the reactions are listed in Table 1. If no change in either the solution or the coupon was noted within 24 hours, the stabilized solution was considered to be non-reactive to the aluminum alloy. A non-stabilized solution of 1-bromopropane reacted with the aluminum coupon within 15 minutes. Analysis of the results listed in Table 1 indicates that as little as 0.01% by weight of dimethyl carbonate was found to inhibit the reaction between the aluminum coupon and 1-bromopropane.

TABLE 1

| Stabilizer | 0.001% | 0.01% | 0.05% | 0.10% | 0.2% |
| --- | --- | --- | --- | --- | --- |
| Dimethyl Carbonate | 1 | 24 | 24 | 24 | 24 |
| Dioxane | 1 | 24 | 24 | 24 | 24 |
| Dioxolane | 1 | 24 | 24 | 24 | 24 |
| Nitromethane | 1 | 24 | 24 | 24 | 24 |
| t-Butanol | 1 | | 2.5 | 24 | 24 |
| Cyclohexene Oxide | 1 | 1 | 24 | | |
| Dimethoxymethane | 1 | 24 | 24 | | |

Reflux Test

The effectiveness of dimethyl carbonate to stabilize refluxing 1-bromo propane in the presence of cleaned aluminum granules was evaluated. Aluminum granules 98+%, 10–30 mesh were cleaned by washing the granules with an 8% by weight aqueous HCl solution. The cleaned aluminum granules were dried and stored under a dry nitrogen atmosphere to prevent formation of an aluminum oxide film. Ten grams of the cleaned aluminum granules were added to 250 ml of 1-bromopropane containing, 2% by weight dimethyl carbonate. The mixture was refluxed for 96 hours. No observable reaction was noted for the stabilized 1-bromopropane solvent.

Co-distillation of 1-Bromopropane and Dimethyl Carbonate

A vapor liquid diagram for 1-bromopropane and dimethyl carbonate was developed by mixing various concentrations of these solvents. These solvent compositions were distilled in a 100 ml Othmer Still. Samples of the vapor and liquid fractions were obtained and analyzed by gas chromatography. The results are listed in Table 2 and are graphically illustrated in FIG. 1. The dimethyl carbonate was observed to co-distill with 1-bromopropane at a concentration from about 1.5% to about 4% by weight.

TABLE 2

| Boiling Point ° C. | Weight Percent of DMC in Liquid Phase | Weight Percent of DMC in Vapor Phase |
| --- | --- | --- |
| 70.7 | 0.31 | 0.26 |
| 70.7 | 0.52 | 0.49 |
| 70.7 | 0.77 | 0.72 |
| 70.7 | 1.03 | 0.92 |
| 70.6 | 1.23 | 1.22 |
| 70.6 | 1.49 | 1.50 |
| 70.6 | 1.91 | 1.75 |
| 70.6 | 2.21 | 1.99 |

TABLE 2-continued

| Boiling Point ° C. | Weight Percent of DMC in Liquid Phase | Weight Percent of DMC in Vapor Phase |
|---|---|---|
| 70.7 | 4.33 | 3.99 |
| 71.0 | 8.77 | 7.28 |

DMC = Dimethyl carbonate

To confirm that an azeotrope composition exists, two additional distillations were performed using a Perkins Elmer Model 151 Annular Still (200 theoretical plates fractionating capability). In the first distillation, 200 grams of stabilized 1-bromopropane solvent containing 2% by weight dimethyl carbonate was distilled. In the second distillation, 200 grams of stabilized 1-bromopropane solvent containing 0.75% by weight dimethyl carbonate was distilled. The results obtained from the distillations are listed in Tables 3 and 4, respectively.

TABLE 3

|  | Weight (g) | Pot Temperature ° C. | Vapor Temperature ° C. | Weight Percent DMC in Distillate |
|---|---|---|---|---|
| Initial | 133.7 | 70.7 | 69.9 | 1.95 |
| Cut 1 | 12.2 | 70.7 | 70.0 | 1.21 |
| Cut 2 | 13.1 | 70.7 | 70.0 | 1.32 |
| Cut 3 | 13.2 | 70.7 | 70.0 | 1.43 |
| Cut 4 | 12.1 | 70.7 | 70.0 | 1.48. |
| Cut 5 | 17.2 | 70.7 | 70.1 | 1.56 |
| Cut 6 | 17.4 | 70.8 | 70.1 | 1.71 |
| Cut 7 | 16.2 | 70.8 | 70.1 | 1.86 |
| Bottoms | 30.1 |  |  | 3.29 |

DMC = Dimethyl carbonate

TABLE 4

| Fractions | Weight (g) | Pot Temperature ° C. | Vapor Temperature ° C. | Weight Percent DMC in Distillate |
|---|---|---|---|---|
| Initial | 200 |  |  | 0.74 |
| Cut 1 | 10.6 | 69.9 | 68.8 | 0.48 |
| Cut 2 | 10.5 | 69.9 | 69.0 | 0.52 |
| Cut 3 | 8.0 | 69.9 | 68.9 | 0.47 |
| Cut 4 | 11.6 | 70.0 | 69.2 | 0.59 |
| Cut 5 | 14.6 | 70.1 | 69.2 | 0.66 |
| Cut 6 | 10.6 | 70.1 | 69.2 | 0.71 |
| Cut 7 | 14.2 | 70.2 | 69.2 | 0.77 |
| Cut 8 | 11.0 | 10.1 | 69.1 | 0.90 |
| Cut 9 |  | 70.5 | 69.1 | 1.12 |
| Bottoms | 3.2 |  |  | 1.91 |

DMC = dimethyl carbonate

While the data listed in Tables 3 and 4 does not indicate an azeotrope exists, only minimal change in the dimethyl carbonate concentration is observed between the vapor and liquid phases of the stabilized solvent. It is apparent from the results that dimethyl carbonate and 1-bromopropane co-distill in a concentration range of about 0–4% by weight.

Resistance of Dialkyl Carbonate to Water Extraction

Stock solutions of stabilized 1-bromopropane solvents were prepared; each solution contained 2% by weight of a single stabilizer. A 75 g aliquot of each solution was combined with 25 g of water, and the mixtures were agitated for 1 minute. The organic phases and aqueous phases were separated and analyzed by gas chromotography to determine the concentrations of the stabilizers in 1-bromopropane and in water. The results are listed in Table 5. Each of the stabilizers examined partitioned between the two phases. Of the stabilizers examined, the dimethyl carbonate concentration in 1-bromopropane decreased the least. The dimethyl carbonate in 1-bromopropane had a water extractability of less than about 10% by weight. These results are indicative of the low partitioning of the dimethyl carbonate into the water phase from 1-bromopropane relative to the other stabilizers. Thus the concentration of dimethyl carbonate in the 1-bromopropane based solvent was not substantially reduced when the solvent was extracted with water.

TABLE 5

| Stabilizer in n-PB | Initial Concentration | Final Concentration | % Decrease |
|---|---|---|---|
| Dimethyl Carbonate | 2.00 | 1.81 | 9 |
| t-Butanol | 2.00 | 0.87 | 56 |
| Dioxolane | 2.00 | 1.46 | 27 |
| Dioxane | 2.00 | 1.28 | 36 |
| Dimethoxymethane | 2.00 | 1.69 | 15 |
| Nitromethane | 2.00 | 1.57 | 21 | n-PB = 1-bromopropane

EXAMPLE 2

1-Bromopropane Stabilized with Dimethyl Carbonate and Butylene Oxide

A series of stabilized solvents having 0.01%, 0.1%, 1%, 6%, 10% by weight stabilizer and an acid scavenger is prepared by separately combining 0.5 g, 5 g, 50 g, 300 g, and 500 g dimethyl carbonate and 0.5 g butylene oxide to a sufficient amount of 1-bromopropane to provide 5 solutions each having a total mass of 5 kg. Each of these 1-bromopropane based stabilized solvents effectively cleans oil-soiled metal parts in a vapor degreasing system without metal induced 1-bromopropane decomposition.

EXAMPLE 3

1- Bromobutane Stabilized with Diethyl Carbonate and Butylene Oxide

A stabilized solvent having 0.1% by weight stabilizer and an acid scavenger is prepared by separately combining 5 g diethyl carbonate and 5 g butylene oxide to a sufficient amount of 1-bromobutane to provide a solution having a total mass of 5 kg. This stabilized solvent effectively cleans oil-soiled metal parts that are completely immersed in a dip tank without metal induced 1-bromobutane decomposition or corrosion of the metal surfaces.

What is claimed is:

1. A stabilized solvent composition comprising $C_3$ to $C_5$ alkyl bromide and between about 0.01% to about 15% by weight of a metal stabilizer system that includes a dialkyl carbonate of the formula $(R_1O)(R_2O)C(O)$ wherein $R_1$ and $R_2$ independently are $C_1$ to $C_4$ alkyl.

2. The composition of claim 1 that includes up to about 4% by weight of the dialkyl carbonate.

3. The composition of claim 2 that includes up to about 2% by weight of the dialkyl carbonate.

4. The composition of claim 1 wherein the dialkyl carbonate is dimethyl carbonate.

5. The composition of claim 1 wherein the dialkyl carbonate is diethyl carbonate.

6. The composition of claim 1 wherein the alkyl bromide is 1-bromopropane.

7. The composition of claim 1 wherein the alkyl bromide is 2-bromopropane.

8. The solvent composition of claim 1 wherein the metal stabilizer system further includes a stabilizer selected from the group consisting of ethers, alcohols, nitroalkanes, epoxides and mixtures thereof.

9. The composition of claim 1 and further comprising about 0.1% to about 5% by weight of an acid scavenger selected from the group consisting of epoxides, amines and mixtures thereof.

10. The composition of claim 1 wherein the alkyl bromide is 1-bromopropane and the dialkyl carbonate is dimethyl carbonate.

11. The solvent composition of claim 10 wherein the metal stabilizer system includes a stabilizer selected from the group consisting of ethers, alcohols, nitroalkanes, epoxides and mixtures thereof.

12. The composition of claim 10 and further comprising about 0.1% to about 5% by weight of an acid scavenger selected from the group consisting of epoxides, amines, and mixtures thereof.

13. A method of cleaning a metal article comprising the step of contacting the article with a solvent composition comprising a $C_3$ to $C_5$ alkyl bromide and between about 0.01% to about 15% by weight of a metal stabilizer system that includes a dialkyl carbonate of the formula $(R_1O)(R_2O)C(O)$ wherein $R_1$ and $R_2$ are independently $C_1$ to $C_4$ alkyl.

14. The method of claim 13 wherein the solvent composition further includes about 0.1% to about 5% of an acid scavenger.

15. The method of claim 13 wherein the metal is selected from the group of metals that are reactive towards $C_3$ to $C_5$ alkyl bromide.

16. The method of claim 13 wherein the solvent composition includes up to about 4% by weight of the dialkyl carbonate.

17. The method of claim 13 wherein the solvent composition includes up to about 2% by weight of the dialkyl carbonate.

18. The method of claim 13 wherein the dialkyl carbonate is dimethyl carbonate.

19. The method of claim 13 wherein the dialkyl carbonate is diethyl carbonate.

20. The method of claim 13 wherein the alkyl bromide is 1-bromopropane.

21. The method of claim 13 wherein the alkyl bromide is 2-bromopropane.

* * * * *

UNITED STATES PATENT AND TRADEMARK OFFICE
CERTIFICATE OF CORRECTION

PATENT NO. : 6,063,749
DATED : May 16, 2000
INVENTOR(S) : DeGroot

Page 1 of 1

It is certified that error appears in the above-identified patent and that said Letters Patent is hereby corrected as shown below:

Column 2,
Line 54, please delete "decreasing" and insert in lieu thereof -- degreasing --.
Line 59, please delete the comma.

Column 4,
Line 51, please delete "solvents" and insert in lieu thereof -- solvent, --.

Column 7,
Line 47, please delete "10.1" and insert in lieu thereof -- 70.1 --.

Signed and Sealed this

Eleventh Day of December, 2001

Attest:

NICHOLAS P. GODICI
Attesting Officer
*Acting Director of the United States Patent and Trademark Office*